(12) United States Patent
Huang

(10) Patent No.: US 9,974,874 B2
(45) Date of Patent: May 22, 2018

(54) MULTI-FUNCTIONAL CUTLERY STERILIZER

(71) Applicant: Anvid Products, Inc., Livermore, CA (US)

(72) Inventor: Weiyuan Huang, Pleasanton, CA (US)

(73) Assignee: Anvid Products, Inc., Livermore, CA (US)

( * ) Notice: Subject to any disclaimer, the term of this patent is extended or adjusted under 35 U.S.C. 154(b) by 0 days. days.

(21) Appl. No.: 15/247,591

(22) Filed: Aug. 25, 2016

(65) Prior Publication Data

US 2017/0360972 A1 Dec. 21, 2017

(30) Foreign Application Priority Data

Jun. 21, 2016 (CN) ..................... 2016 2 0631351 U

(51) Int. Cl.
*A61L 2/10* (2006.01)
*A61L 2/04* (2006.01)
*H05B 1/02* (2006.01)
*A61L 2/24* (2006.01)

(52) U.S. Cl.
CPC ...... *A61L 2/10* (2013.01); *A61L 2/24* (2013.01); *H05B 1/0205* (2013.01); *A61L 2202/11* (2013.01); *A61L 2202/14* (2013.01)

(58) Field of Classification Search
CPC ..... A61L 2/00; A61L 2/08; A61L 2/10; A61L 2202/00; A61L 2202/10; A61L 2202/20
USPC ............... 250/453.11, 454.11, 455.11, 493.1, 250/504 R; 422/22, 24
See application file for complete search history.

(56) References Cited

U.S. PATENT DOCUMENTS

| | | | | |
|---|---|---|---|---|
| 2003/0066971 | A1* | 4/2003 | Yen ......................... | A47J 47/16 250/455.11 |
| 2003/0131426 | A1* | 7/2003 | Schulling ................ | A47L 21/04 15/21.1 |
| 2005/0230639 | A1* | 10/2005 | Ancona ..................... | A61L 2/10 250/455.11 |
| 2009/0255133 | A1* | 10/2009 | Bonapace .............. | A47G 21/14 30/298.4 |

* cited by examiner

*Primary Examiner* — Nicole Ippolito
(74) *Attorney, Agent, or Firm* — Sheppard Mullin Richter & Hampton LLP

(57) ABSTRACT

A multi-functional cutlery sterilizer, having a heating panel and a heating tube, operable via a press button panel of a main control device, so that the sterilization chamber can reach a high temperature to achieve sterilization. Also, a UV sterilization device is provided; by placing cutlery in the sterilization chamber and operating the UV sterilization device via the press button panel, UV light will illuminate and achieve UV sterilization. The cutlery sterilizer is additionally provided with UV sterilization, thereby providing an additional means for sterilization and thus equipping itself with more powerful functions. The sterilizer can sterilize cutlery made of different materials and therefore has a wider applicability. Further, cutlery not suitable for high temperature sterilization can be sterilized by UV sterilization. Therefore, even more cutlery made of more different materials can now be sterilized, thereby further widening the applicability of the sterilizer and facilitating sterilization of special cutlery.

7 Claims, 3 Drawing Sheets

MULTI-FUNCTIONAL CUTLERY STERILIZER

CROSS-REFERENCE TO RELATED APPLICATION

This application claims the benefit under 35 U.S.C. § 119 of Chinese Application No. 201620631351.7, filed Jun. 21, 2016. The content of this application is incorporated by reference into the present disclosure in its entirety.

BACKGROUND

The present invention relates to a multi-functional cutlery sterilizer. Ultraviolet sterilization damages the molecular structures of DNA or RNA of germs and bacteria by using UV rays emitted from a UV light, thereby causing the death of growth cells and regenerative cells and thus achieving the effect of sterilization and disinfection.

Nowadays, cutlery sterilization is often achieved by high temperature sterilization. However, cutlery sterilizers available nowadays are mono-functional since they can only sterilize limited types of cutlery. In fact, most of them can only sterilize cutlery made of one particular type of material, thereby having much limitation during actual use. Also, most of them do not support bactericidal function, and thus do not facilitate sterilization of special cutlery.

SUMMARY

One embodiment of present disclosure provides a multi-functional cutlery sterilizer, comprising a shell; wherein a sterilization chamber is provided inside the shell; cutlery insertion slots are provided on the shell for inserting cutlery into the sterilization chamber; a main control device is provided in the sterilization chamber; and the main control device is electrically connected with a high-temperature heating device and a UV sterilization device.

Preferably, the high-temperature heating device comprises a heating panel; a heating tube is welded on the heating panel; the heating tube is electrically connected with the main control device via a temperature controller.

Preferably, the heating tube is provided with a thermal fuse.

Preferably, the UV sterilization device comprises a light base supporter; two ends of the light base supporter are disposed with two UV light bases respectively; a UV light is mounted via the two UV light bases; the UV light is electrically connected with the main control device; a light shade is provided along an illuminating direction of the UV light.

Preferably, the main control device comprises a main control panel and a press button circuit board which transmits control commands to the main control panel; several press buttons are provided on the press button circuit board; each of the press buttons is provided with a press button indicative light shade; each of the press button indicative light shade 13 is embedded on the shell.

Preferably, the shell comprises an upper shell, a middle shell and a lower shell; the cutlery insertion slots are provided on the upper shell; a cover plate is provided on the cutlery insertion slots.

The lower shell is also provided with an indicative light shade; an indicative light indicating a working condition of the UV sterilization device is provided inside the indicative light shade.

Preferably, a left cover and a right cover are provided in the sterilization chamber; the left cover and/or the right cover is/are provided with installation holes and guidance slots for fixing the high-temperature heating device.

The present invention has the following advantages compared with the prior arts: The multi-functional cutlery sterilizer is provided with a heating panel and a heating tube to create high temperature heat flow, and is operable via a press button, so that the sterilization chamber can reach a high temperature quickly to achieve sterilization. Also, a UV sterilization device is provided, so that by placing cutlery items in the sterilization chamber and operating the UV sterilization device via the press button panel, the UV light will illuminate and emit UV rays to achieve UV sterilization. The cutlery sterilizer of the present invention is additionally provided with UV sterilization, thereby providing an additional means for sterilization and thus rendering the present invention more powerful in its functions. The sterilizer of the present invention can sterilize cutlery made of different materials and so it has wider applicability. Further, cutlery not suitable for high temperature sterilization can be sterilized by UV sterilization. Therefore, even more cutlery made of more different materials can now be sterilized, thereby further widening the applicability of the present invention and facilitating sterilization of special cutlery.

BRIEF DESCRIPTION OF THE DRAWINGS

The drawings described herein are intended for further understanding of the present invention. The drawings form a part of the present application, but should not be considered improperly limiting the present invention.

DETAILED DESCRIPTION

The present invention is further described in detail below with reference to the drawings and an embodiment. The embodiment described herein is for illustrative purpose only in order to explain the present invention, and thus should not limit the present invention.

Figure 1:
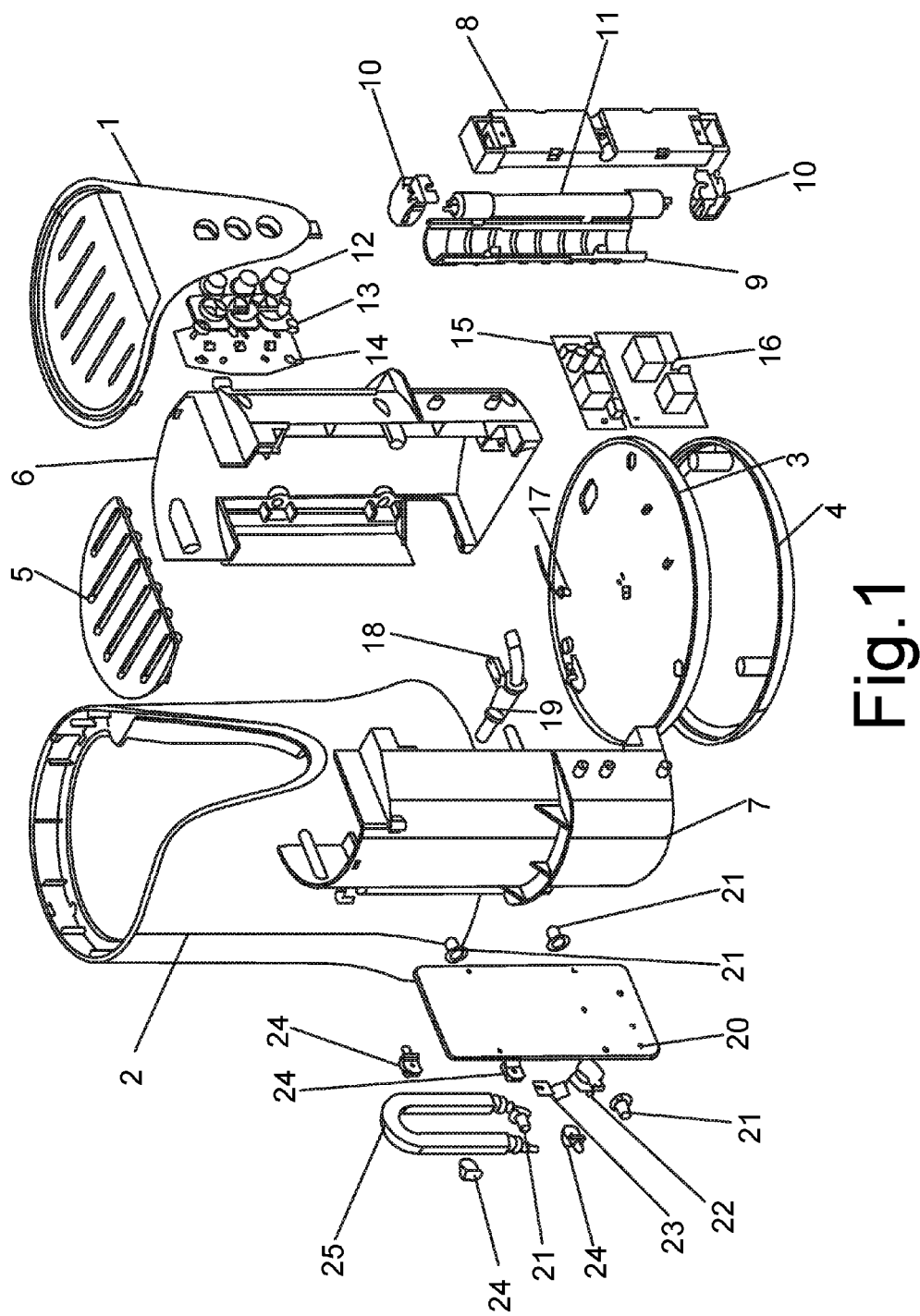
FIG. 1 is a structural view of an embodiment of the present invention in a to-be-assembled condition.
Figure 2:
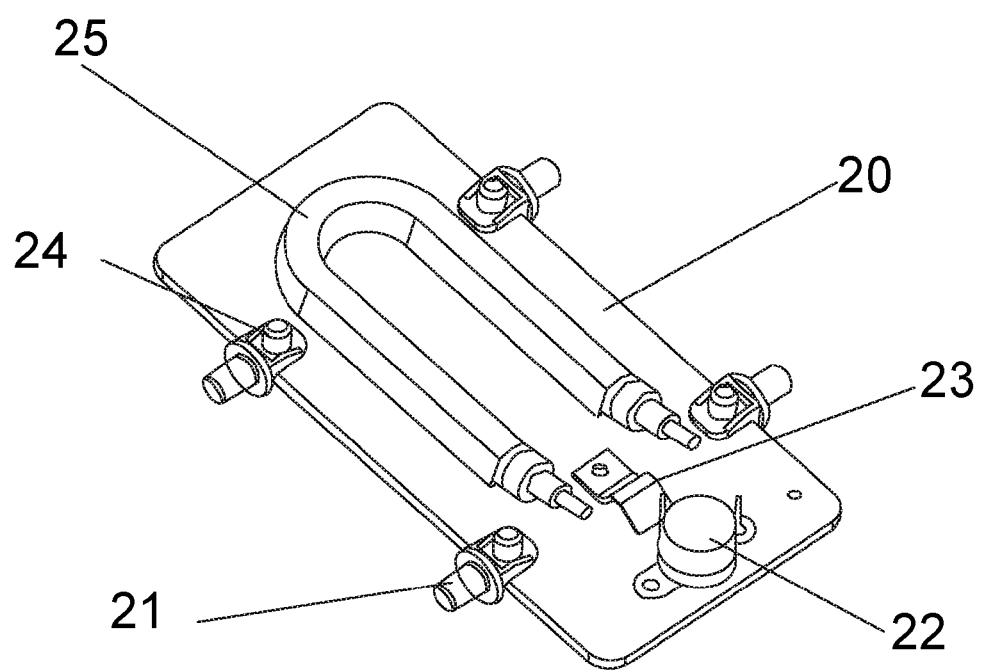
FIG. 2 is a structural view of the high-temperature heating device according to an embodiment of the present invention.
Figure 3:
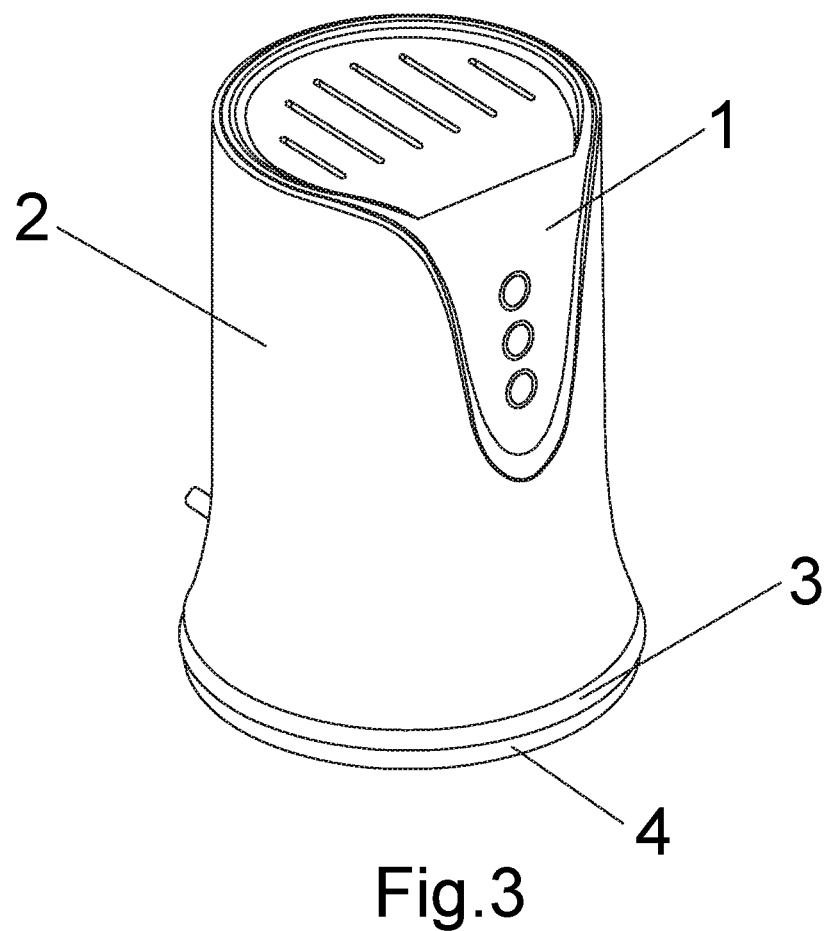
FIG. 3 is a structural view of an embodiment of the present invention.

As shown in FIGS. 1-3, a multi-functional cutlery sterilizer comprises a shell; a sterilization chamber is provided inside the shell; the shell comprises an upper shell 1, a middle shell 2 and a lower shell 4; cutlery insertion slots are provided on the upper shell 1; a cover plate 5 is provided on the cutlery insertion slots; a main control device is provided in the sterilization chamber; the main control device is electrically connected with a mains power source via a power line 19; the power line 19 is fixed on the lower shell 4 via a wire fixation plate 18; the main control device is electrically connected with a high-temperature heating device and a UV sterilization device.

The high-temperature heating device comprises a heating panel 20 made of aluminum board; a heating tube 25 is welded on the heating panel 20; the heating tube 25 is electrically connected with the main control device via a temperature controller 22.

A modified version of the present embodiment also comprises a thermal fuse for the heating tube 25; the thermal fuse is tightly attached to the heating panel 20 via a fuse fixation lock 23; the thermal fuse prevents safety hazards caused by excessively high temperature of the heating tube 25 or the heating panel 20.

In the present embodiment, the UV sterilization device comprises a light base supporter 8; two ends of the light base supporter 8 are disposed with two UV light bases 10 respectively; a UV light 11 is mounted via the two UV light bases 10; the UV light 11 is electrically connected with the main control device; a light shade 9 is provided along an illuminating direction of the UV light 11.

In the present embodiment, the main control device comprises a main control panel 16 and a press button circuit board 14 which transmits control commands to the main control panel 16; several press buttons 12 are provided on the press button circuit board 14; each of the press buttons 12 is provided with a press button indicative light shade 13, including a power-on indicative light shade, a heating indicative light shade and a sterilization indicative light shade; each of the press button indicative light shade 13 is embedded on the shell.

The lower shell 4 is also provided with an indicative light shade 3; an indicative light 17 indicating a working condition of the UV sterilization device is provided inside the indicative light shade 3.

In the present embodiment, a left cover 7 and a right cover 6 are provided in the sterilization chamber; the left cover 7 and/or the right cover 6 is/are provided with installation holes and guidance slots; the high-temperature heating device is fixed via the installation holes, the guidance slots and mounting attachments 24 at two sides of the heating panel 20; a silicon sleeve 21 is provided at an outer side of each of the mounting attachments 24.

The technical solution provided by an embodiment of the present invention is described in detail above. Specific examples are used for explaining the principle and implementation of the embodiment of the present invention. The embodiment described herein is only intended to assist in understanding the principle of the embodiment of the present invention. A person skilled in this field of art may make changes to the embodiment and the field of application of the present invention on the basis of the teachings of the present invention. In summary, the above description should not limit the present invention.

The invention claimed is:

1. A multi-functional cutlery sterilizer, comprising a shell; a sterilization chamber disposed in the shell; a plurality of cutlery insertion slots disposed on the shell for inserting one or more cutlery items into the sterilization chamber for sterilization; and a main control device electrically connected with a heating device and a UV sterilization device in the shell.

2. The multi-functional cutlery sterilizer as in claim 1, wherein the heating device comprises a heating panel and a heating tube welded on the heating panel wherein the heating tube is electrically connected with the main control device via a temperature controller.

3. The multi-functional cutlery sterilizer as in claim 2, further comprising a thermal fuse electrically connected to the heating tube.

4. The multi-functional cutlery sterilizer as in claim 1, wherein the UV sterilization device comprises
   a light base supporter;
   two UV light bases each being connectable to each of two ends of the light base supporter;
   a UV light mounted via the two UV light bases and electrically connected to the main control device; and
   a light shade disposed along an illuminating direction of the UV light.

5. The multi-functional cutlery sterilizer as in claim 1, wherein the main control device comprises
   a main control panel;
   a press button circuit board which transmits control commands to the main control panel;
   a plurality of press buttons disposed on the press button circuit board; and
   an indicative light shade around each of the press buttons.

6. The multi-functional cutlery sterilizer as in claim 1, wherein the shell comprises an upper shell, a middle shell and a lower shell; the cutlery insertion slots are provided on the upper shell; a cover plate is provided on the cutlery insertion slots; the lower shell is also provided with an indicative light shade; and an indicative light indicating a working condition of the UV sterilization device is provided inside the indicative light shade.

7. The multi-functional cutlery sterilizer as in claim 1, wherein a left cover and a right cover are provided in the sterilization chamber; and the left cover and/or the right cover is/are provided with installation holes and guidance slots for fixing the heating device.

* * * * *